United States Patent [19]
Roberts

[11] Patent Number: 5,470,951
[45] Date of Patent: Nov. 28, 1995

[54] PEPTIDES FOR ANTAGONIZING THE EFFECTS OF AMYLOID βPROTEIN

[75] Inventor: Eugene Roberts, Monrovia, Calif.

[73] Assignee: City of Hope, Duarte, Calif.

[21] Appl. No.: 127,904

[22] Filed: Sep. 29, 1993

[51] Int. Cl.$^6$ .............................. A61K 38/00; C07K 5/00; C07K 7/00; C07K 17/00
[52] U.S. Cl. .................................................. 530/330
[58] Field of Search ............................ 530/330; 514/17, 514/18

[56] References Cited

PUBLICATIONS

Cecil Textbook of Medicine, 19th Ed. eds. Wyngaarden/Smith/Bennett, 1992 pp. 2076–2077.

*Primary Examiner*—Jill Warden
*Assistant Examiner*—Sheela J. Huff
*Attorney, Agent, or Firm*—Edward S. Irons

[57] ABSTRACT

Three non-amnestic and non-memory enhancing peptides, Asp Phe Phe Val Gly (SEQ ID NO: 1), Gln Phe Val Gly (SEQ ID NO: 2), and Ala Ile Phe Thr (SEQ ID NO: 3), that block the effects of β-(12–28), a peptide homologous to amyloid β protein (Aβ) are disclosed. This invention relates to amelioration of amnesia and other neurotoxicitiy in Alzheimer disease (AD) caused by deposition of Aβ and, therefore, relates to attenuation of the disease process and consequential improvement of the quality of life for individuals suffering from AD.

4 Claims, 1 Drawing Sheet

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
    ( A ) LENGTH: 5
    ( B ) TYPE: Amino Acid
    ( C ) STRANDEDNESS:
    ( D ) TOPOLOGY: Unknown ( x i ) SEQUENCE DESCRIPTION: SEQ ID NO: 1:

Asp  Phe  Phe  Val  Gly
       1                    5

( 2 ) INFORMATION FOR SEQ ID NO: 2:

( i ) SEQUENCE CHARACTERISTICS:
    ( A ) LENGTH: 4
    ( B ) TYPE: Amino Acid
    ( C ) STRANDEDNESS:
    ( D ) TOPOLOGY: Unknown ( x i ) SEQUENCE DESCRIPTION: SEQ ID NO: 2:

Gln  Phe  Val  Gly
       1

( 2 ) INFORMATION FOR SEQ ID NO: 3:

( i ) SEQUENCE CHARACTERISTICS:
    ( A ) LENGTH: 4
    ( B ) TYPE: Amino Acid
    ( C ) STRANDEDNESS:
    ( D ) TOPOLOGY: Unknown ( x i ) SEQUENCE DESCRIPTION: SEQ ID NO: 3:

Ala  Ile  Phe  Thr
       1

( 2 ) INFORMATION FOR SEQ ID NO: 4:

( i ) SEQUENCE CHARACTERISTICS:
    ( A ) LENGTH: 2
    ( B ) TYPE: Amino Acid
    ( C ) STRANDEDNESS:

(D) TOPOLOGY: Unknown (xi) SEQUENCE DESCRIPTION: SEQ ID NO: 4:

Phe Phe
1

(2) INFORMATION FOR SEQ ID NO: 5:

(i) SEQUENCE CHARACTERISTICS:
(A) LENGTH: 2
(B) TYPE: Amino Acid
(C) STRANDEDNESS:
(D) TOPOLOGY: Unknown (xi) SEQUENCE DESCRIPTION: SEQ ID NO: 5:

Val Val
1

(2) INFORMATION FOR SEQ ID NO: 6:

(i) SEQUENCE CHARACTERISTICS:
(A) LENGTH: 3
(B) TYPE: Amino Acid
(C) STRANDEDNESS:
(D) TOPOLOGY: Unknown (xi) SEQUENCE DESCRIPTION: SEQ ID NO: 6:

Ala Val Phe
1

(2) INFORMATION FOR SEQ ID NO: 7:

(i) SEQUENCE CHARACTERISTICS:
(A) LENGTH: 3
(B) TYPE: Amino Acid
(C) STRANDEDNESS:
(D) TOPOLOGY: Unknown (xi) SEQUENCE DESCRIPTION: SEQ ID NO: 7:

Phe Val Phe
1

(2) INFORMATION FOR SEQ ID NO: 8:

(i) SEQUENCE CHARACTERISTICS:
(A) LENGTH: 4
(B) TYPE: Amino Acid
(C) STRANDEDNESS:
(D) TOPOLOGY: Unknown (xi) SEQUENCE DESCRIPTION: SEQ ID NO: 8:

Ala Phe Ile Gly
1

(2) INFORMATION FOR SEQ ID NO: 9:

(i) SEQUENCE CHARACTERISTICS:
(A) LENGTH: 4
(B) TYPE: Amino Acid
(C) STRANDEDNESS:
(D) TOPOLOGY: Unknown (xi) SEQUENCE DESCRIPTION: SEQ ID NO: 9:

Gly Phe Met Thr
1

(2) INFORMATION FOR SEQ ID NO: 10:

```
        ( i ) SEQUENCE CHARACTERISTICS:
              ( A ) LENGTH: 4
              ( B ) TYPE: Amino Acid
              ( C ) STRANDEDNESS:
              ( D ) TOPOLOGY: Unknown ( x i ) SEQUENCE DESCRIPTION: SEQ ID NO: 10:

Asn   Leu   Ile   Thr
               1
```

( 2 ) INFORMATION FOR SEQ ID NO: 11:

```
        ( i ) SEQUENCE CHARACTERISTICS:
              ( A ) LENGTH: 4
              ( B ) TYPE: Amino Acid
              ( C ) STRANDEDNESS:
              ( D ) TOPOLOGY: Unknown ( x i ) SEQUENCE DESCRIPTION: SEQ ID NO: 11:

Ser   Phe   Phe   Gly
               1
```

( 2 ) INFORMATION FOR SEQ ID NO: 12:

```
        ( i ) SEQUENCE CHARACTERISTICS:
              ( A ) LENGTH: 4
              ( B ) TYPE: Amino Acid
              ( C ) STRANDEDNESS:
              ( D ) TOPOLOGY: Unknown ( x i ) SEQUENCE DESCRIPTION: SEQ ID NO: 12:

Ser   Phe   Val   Gly
               1
```

( 2 ) INFORMATION FOR SEQ ID NO: 13:

```
        ( i ) SEQUENCE CHARACTERISTICS:
              ( A ) LENGTH: 4
              ( B ) TYPE: Amino Acid
              ( C ) STRANDEDNESS:
              ( D ) TOPOLOGY: Unknown ( x i ) SEQUENCE DESCRIPTION: SEQ ID NO: 13:

Asp   Phe   Phe   Val
               1
```

( 2 ) INFORMATION FOR SEQ ID NO: 14:

```
        ( i ) SEQUENCE CHARACTERISTICS:
              ( A ) LENGTH: 7
              ( B ) TYPE: Amino Acid
              ( C ) STRANDEDNESS:
              ( D ) TOPOLOGY: Unknown ( x i ) SEQUENCE DESCRIPTION: SEQ ID NO: 14:

Lys   Leu   Val   Phe   Phe   Ala   Glu
               1                       5
```

( 2 ) INFORMATION FOR SEQ ID NO: 15:

```
        ( i ) SEQUENCE CHARACTERISTICS:
              ( A ) LENGTH: 5
              ( B ) TYPE: Amino Acid
              ( C ) STRANDEDNESS:
              ( D ) TOPOLOGY: Unknown ( x i ) SEQUENCE DESCRIPTION: SEQ ID NO: 15:
```

-continued

```
Lys  Leu  Val  Phe  Phe
 1                   5
```

PEPTIDES FOR ANTAGONIZING THE EFFECTS OF AMYLOID βPROTEIN

FIELD OF THE INVENTION

This invention relates to amelioration of amnesia in Alzheimer disease (AD) caused by deposition of amyloid β protein (Aβ) and, therefore, to attenuation of the disease process and consequential improvement of the quality of life for individuals suffering from AD. More particularly the invention relates to prevention of deterioration of memory and quality of life in AD patients by administration of the peptides Asp Phe Phe Val Gly (SEQ ID NO: 1), Gln Phe Val Gly (SEQ ID NO: 2), and Ala Ile Phe Thr (SEQ ID NO: 3) or amides or esters thereof. Administration of these substances to human individuals with AD can enhance memory and attenuate progression of the disease, in this way improving the quality of life.

DEFINITIONS

The following abbreviations are used:
Aβ=amyloid β protein
FAAT=footshock active avoidance training
ICV=intracerebroventricular
Ala=alanine
Cys=cysteine
Asp=aspartic acid
Glu=glutamic acid
Phe=phenylalanine
Gly=glycine
His=histidine
Ile=isoleucine
Lys=lysine
Leu=leucine
Met=methionine
Asn=asparagine
Pro=proline
Gln=glutamine
Arg=arginine
Ser=serine
Thr=threonine
Val=valine
Trp=tryptophan
Tyr=tyrosine

BACKGROUND OF THE INVENTION

Much data suggests that in Alzheimer disease (AD) there may be genetically and/or environmentally induced defects in the enzymatic machinery involved in degradation of amyloid precursor protein (APP) (for reviews, see refs. 1 and 2). Alternative splicing of mRNAs gives rise to at least five forms of APP, two of which possess a Kunitz-type protease inhibitory domain. Normal lysosomal processing of APPs involves highly coordinated sequences of desulfation, dephosphorylation, deglycosylation, and proteolytic splitting. The APPs may belong to a family of polypeptide precursors or polyproteins that upon processing give rise to a number of different bioactive peptides that may act individually or in concert to regulate cellular activation (3–5). The processing of the parent molecules and/or the extracellular secretion of the resulting subunits may vary with species, tissue, age, hormonal status, extent of phosphorylation (6), etc. Although the APPs may be cell-surface receptors (7, 8), some of the peptidic fragments derived from them may be ligands (9) for specific membrane sites.

To some extent in normal aging and to greater extent in AD and in adult Down syndrome, abnormal processing of APP gives rise to an insoluble self-aggregating 42-amino acid polypeptide designated as amyloid β protein (Aβ) that is found in amyloid (10–14). The extent of Aβ deposition correlates with the degree of neuronal damage, cognitive impairment, and memory loss (15–18). Amyloid-like fibrils arise readily in vitro under physiological conditions even from the following smaller peptides homologous to Aβ: β-(1–28) (N-terminus residues 1 to 28), [Gln$^{11}$]β-(1–28), β-(12–18), and β-(18–28) (19–21). Extensive stacks of β-pleated sheets are formed from the latter peptide (21). Functional deficits arise in AD from damage to nerve circuitry per se, which is known to occur in late phases of the disease (22, 23). It also is possible that binding of Aβ and related peptides to components of the extracellular matrix (e.g., proteoglycans (24)) or to receptors on endothelial, glial, or neuronal cells in particular brain regions could have disruptive effects on neuronal communications at earlier stages of the disease when the deposits of these substances are diffused and typical cytopathologiocal evidence of AD often is absent.

It has been demonstrated (25) that Aβ and, perhaps, smaller peptidic fragments thereof that are responsible for binding of Aβ to cell membranes or components of the extracellular matrix may have amnestic effects upon appropriate administration to experimental animals. Hence, soluble peptides or structurally mimetic nonpeptidic substances can be devised to antagonize the binding of the Aβ and thus alleviate some of the symptoms of AD not caused b actual physical destruction of neural circuitry. Progression may also be attenuated by such substances.

SUMMARY OF THE INVENTION

This invention involves the discovery that three peptides, Asp Phe Phe Val Gly (SEQ ID NO: 1), Gln Phe Val Gly (SEQ ID NO: 2), and Ala Ile Phe Thr (SEQ ID NO: 3), overcome the amnestic effects of β-(12–28), a peptide homologous to Aβ that is as potently amnestic as Aβ (25) and which shows amyloid-like aggregation similarly to Aβ (19–21). No other substances are known which serve this purpose.

DETAILED DESCRIPTION OF THE INVENTION

Screening of various peptides which neither are significantly amnestic nor memory-enhancing in memory-testing paradigms in mice resulted in the discovery of three peptides that blocked the amnestic effects of β-(12–28), a peptide homologous to Aβ. Administration of the peptides (SEQ ID NO: 1, SEQ ID NO: 2, SEQ ID NO: 3) or their esters or amides orally, subcutaneously, intravenously, transcutaneously, intrathecally, sublingually, rectally, or intracisternally leads to an amelioration of symptoms in Alzheimer disease by decreasing deposition of amyloid in the brain.

This discovery facilitates the development of substances that can antagonize binding of Aβ to neural structure and thus attenuate symptoms and progression of Alzheimer disease. Similarity in brain function in various mammals, including human beings, and previous neurological experience, indicates that the three peptides discovered to block the amnestic effects of β-(12–28) and derivatives and variants including esters and amides thereof will be effective therapeutic substances in human beings with Alzheimer disease. In no known instance have such substances been proposed for this purpose.

EXEMPLIFICATION OF THE INVENTION

Materials and Methods

Figure 1:
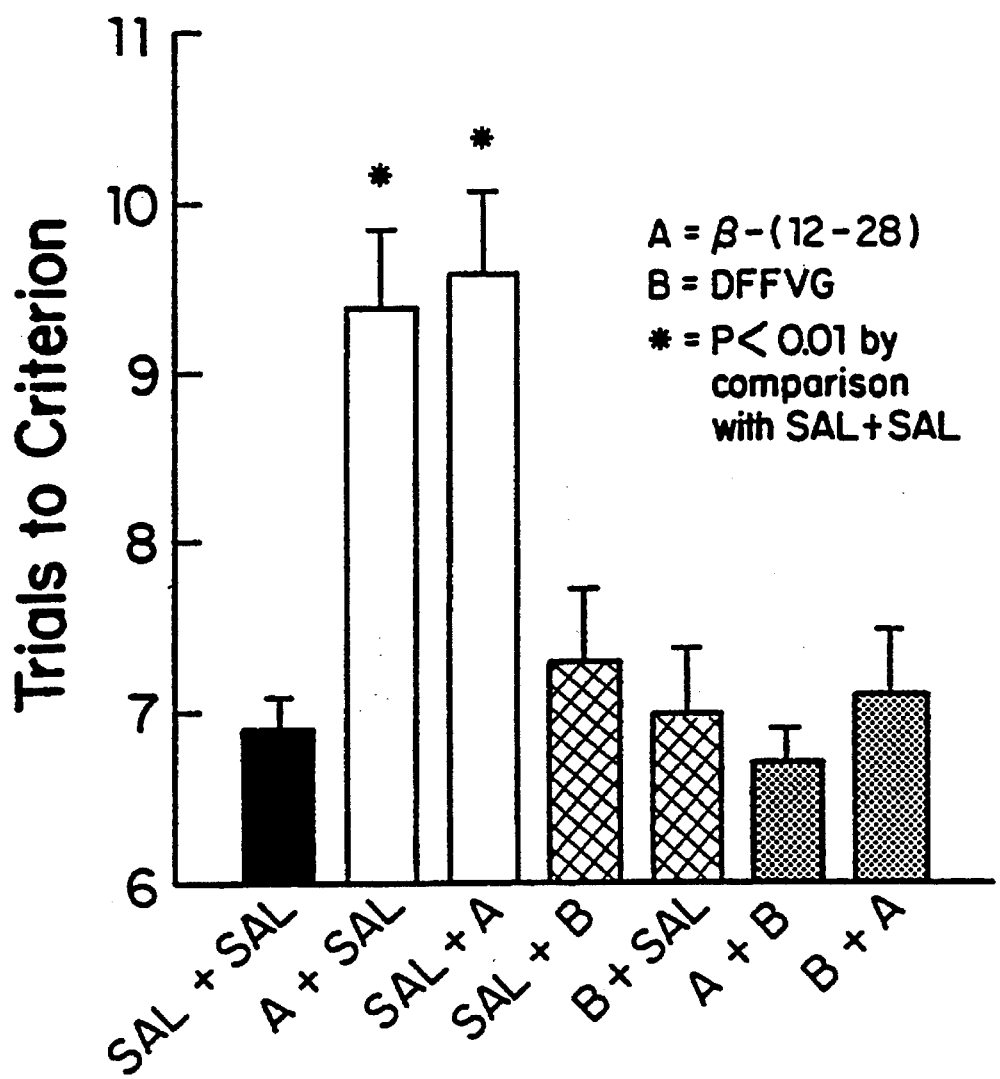
FIG. 1 depicts an antagonism by Asp Phe Phe Val Gly (SEQ ID NO: 1) of amnestic effect of β-(12–28) when administered before or after β-(12–28) to groups of 15 mice each. SAL=physiological saline (sterile).

Test Animals. After one week in the laboratory, CD-1 male mice obtained from Charles River Breeding Laboratories were caged individually 24–28 hours prior to training and remained singly housed until retention was tested one week later. Animal rooms were on a 12-hour light/dark cycle with lights going on at the hour of 0600. Median body weight was 35 g, with a range of 33–38 g. Mice were assigned randomly to groups of ten in the experiments reported in Table 1, groups of 14 in the experiments reported in Table 2, and groups of 15 in FIG. 1 and were trained and tested between the hours of 0700 and 1500.

Peptides Tested. The peptides used in these studies were synthesized and analyzed to establish purity by standard methods at the Beckman Research Institute.

Peptides were dissolved in 8% vol/vol dimethyl sulfoxide and diluted to a final concentration of 0.001% dimethyl sulfoxide in saline. Upon testing for retention of FAAT after receiving post-training ICV administration of 2 µl of the above vehicle the mean numbers of trials to criterion±standard error of the mean (SEM for well trained mice and weakly trained mice were 6.85±0.20 and 9.07±0.25, respectively (see the paragraph below for definition of the two training paradigms).

The experiments below tested whether or not there were amnestic or memory-enhancing effects at 6 nmol of peptide per mouse.

Apparatus, training and Testing Procedures. The T-maze used for footshock active avoidance training (FAAT) consisted of a black plastic alley (46 cm long) with a start box at one end and two goal boxes (17.5 cm long) at the other. The start box was separated from the alley be a plastic guillotine door that prevented movement down the alley until training began. The alley was 12.5 cm deep and 9.8 cm wide. An electrifiable stainless steel rod floor ran throughout the maze.

Mice were not permitted to explore the maze before training. A block of training trials began when a mouse was placed in the start box. The guillotine door was raised and a muffled doorbell-type buzzer sounded simultaneously; footshock was 5 seconds later through a scrambled grid floor shocker (Colbourn Instruments, Model E13-08). The goal box first entered during the first set of trials was designated as "incorrect", and footshock was continued until the mouse entered the other goal box, which in all subsequent trials was designated "correct" for the particular mouse. At the end of each group of trials, the mouse was removed to its home cage.

As training proceeded, a mouse made one of two types of responses. A response latency longer than 5 seconds was classed as an escape from the footshock. A response latency less than or equal to 5 seconds was considered an avoidance, since the mouse avoided receiving a footshock. Two exclusion criteria were applied to reduce learning variability among mice, as follows. On the first training trials, mice with escape latencies greater than 20 seconds were discarded. Mice not having at least one errorless escape latency between 1.5 and 3.5 seconds on training trials 3 or 4 were excluded. The total exclusions were fewer than 15%. Mice received five such training trials. One week after training and post-trial administration of vehicle alone or vehicle containing test substance, T-maze training was resumed until each mouse made five avoidance responses in six consecutive training trials (trials to criterion). The recall score was taken to be the percentage of tested mice remembering original training.

Well-trained animals (recall score approximately 80%) were used to determine whether or not administered substances could cause amnesia. In these instances, training was performed under conditions that tend to maximize learning (sound intensity, 65 decibels; footshock current, 0.35 mA; intertrial interval, 45 seconds). In the cases in which it was desired to detect whether or not there was an enhancing effect on memory, training conditions were adjusted so that the initial recall score in vehicle controls was only approximately 20% (sound intensity, 55 decibels; footshock current, 0.30 mA; intertrial interval, 30 seconds).

Surgical Procedure in Preparation for Intracerebroventricular (ICV) Administration of Substances ICV injection was the mode of administration of test substances because this eliminates problems of differential penetration of the blood-brain barrier. The following procedure was performed 24–48 hours prior to training. A single hole was drilled through the skull over the third ventricle (−0.5 mm relative to bregma, 0.5 mm right of central suture) while the mouse, appropriately anesthetized with methoxyflurane, was held in a stereotaxic instrument. The third ventricle was chosen as site of ICV drug injection because only a single injection is required and the drug quickly reaches limbic system structures, believed to be associated with memorial processes. Immediately after training, mice were anesthetized with enflurane, a short acting anesthetic, and given an ICV injection of 2 µl of vehicle alone or test substance in vehicle delivered over a 30-second period through a 31-gauge needle attached to a 10-µl syringe; the injection was given within 2–3 minutes after the training. Accuracy of injection was determined to be greater than 95% by due injection, monitored regularly.

Statistical Treatment of Data. All of the results are expressed in terms of the mean and standard errors of the mean (SEM). Significance of overall effects of treatment was determined by one-way analysis of variance (ANOVA) run on trials to criterion. Dunnett's t-test was used to make multiple comparison of individual test groups with control groups. See Bruning, J. E., et al., in *Computational Handbook of Statistics*, 2d ed., Scott, Foreman and Co., Glenview, pp. 18–30, 122–124, 128–130 (1977). Statistical comparison among experimental groups were made by Bukey's t-test. See Winer, B. J., *Statistical Principles in Experimentation Design*, 2d ed., McGraw-Hill, New York, pp. 196–210, 397–402 (1971).

RESULTS

Three non-amnestic peptides block the amnestic effects of β-(12–28), a peptide homologous to β/A4). The following peptides tested under standard conditions in groups of 15 mice. Each were found to have no significant amnestic effect in the standard test with well-trained mice: Phe Phe (SEQ ID NO: 4), Val Val (SEQ ID NO: 5), Ala Val Phe (SEQ ID NO: 6), Phe Val Phe (SEQ ID NO: 7), Ala Phe Ile Gly (SEQ ID NO: 8), Ala Ile Phe Thr (SEQ ID NO: 3), Gly Phe Met Thr (SEQ ID NO: 9), Asn Leu Ile Thr (SEQ ID NO: 10), Gln Phe Val Gly (SEQ ID NO: 2), Ser Phe Phe Gly (SEQ ID NO: 11), Ser Phe Val Gly (SEQ ID NO: 12), Asp Phe Phe Val (SEQ ID NO: 13), Asp Phe Phe Val Gly (SEQ ID NO: 1), Lys Leu Val Phe Phe Ala Glu (SEQ ID NO: 14), and Lys Leu Val Phe (SEQ ID NO: 15). Three of the above, SEQ ID NOS: 1, 2 and 3, blocked the amnestic effect of β-(12–28) (26) on retention of FAAT when co-administered to groups of ten mice, each with isomolar amounts (6 nmol) of β-(12–28) (Table 1), giving the following values for trials to criterion ±SEM and p values for comparison with β-(12–28): β-(12–28) alone, 9.62+0.30; with Gln Phe Val Gly (SEQ ID NO: 2), 6.69±0.22, p<0.01; with Asp Phe Phe Val Gly (SEQ ID NO: 1), 6.80±0.38, p<0.01; and with Ala Ile Phe Thr (SEQ ID NO: 3), 6.92±0.32, p<0.01.

Effects of ICV co-administered non-amnestic peptides on amnestic effects of β-(12-28) on retention of FAAT using groups of ten mice

| Peptide | Trial to criterion, no (mean + SEM)[1] | P-value for comparison with β-(12-28) alones |
|---|---|---|
| Vehicle alone | 6.85 ± 0.20 | — |
| β-(12-28) alone | 9.62 ± 0.30[2] | — |
| β-(12-28) + Ala Val Phe | 9.31 ± 0.36 | NS[4] |
| β-(12-28) + Asp Phe Phe Val | 9.31 ± 0.38 | NS |
| β-(12-28) + Lys Leu Val Phe Phe | 9.23 ± 0.34 | NS |
| β-(12-28) + Asn Leu Ile Thr | 9.15 ± 0.41 | NS |
| β-(12-28) + Lys Leu Val Phe Phe Ala Glu | 9.08 ± 0.30 | NS |
| β-(12-28) + Phe Val Phe | 8.92 ± 0.26 | NS |
| β-(12-28) + Ala Phe Ile Glv | 8.92 ± 0.38 | NS |
| β-(12-28) + Val Val | 8.85 ± 0.42 | NS |
| β-(12-28) + Ser Phe Val Gly | 8.85 ± 0.41 | NS |
| β-(12-28) + Gly Phe Met Thr | 8.85 ± 0.47 | NS |
| β-(12-28) + Phe Phe | 8.69 ± 0.46 | NS |
| β-(12-28) + Ser Phe Phe Gly | 8.08 ± 0.40 | NS |
| β-(12-28) + Ala Ile Phe Thr | 6.92 ± 0.32 | <0.01 |
| β-(12-28) + Asp Phe Phe Val Gly | 6.80 ± 0.38 | <0.01 |
| β-(12-28) + Gln Phe Val Gly | 6.69 ± 0.22 | <0.01 |

[1]The higher the mean the less the efficacy of a peptide in blocking the amnestic effect of B-(12-28).
[2]P<0.01 for comparison with vehicle alone.
[3]P values were obtained for selected comparisons using Tukey's t-test after obtaining a significant F value by analysis of variance (ANOVA).
[4]NS= not significant.

Subsequently Asp Phe Phe Val Gly (SEQ ID NO: 1) and β-(12–28) were given ICV separately post-training before or after saline (2 μl each, 60 seconds apart) or first Asp Phe Phe Val Gly (SEQ ID NO: 1) and then β-(12–28) or first β-(12–28) and then Asp Phe Phe Val Gly (SEQ ID NO: 1) (FIG. 1). Whether saline was given before or after β-(12–28) did not affect the result, indicating that increase of total volume administered ICV from 2 μl to 4 μl did ot matter. The order of administration of β-(12–28) and Asp Phe Phe Val Gly (SEQ ID NO: 1) did not affect the ability of the latter to block the amnestic effect of the former (FIG. 1). These latter results suggest, but do not prove, that direct interaction of the counter-amnestic peptides with β-(12–28) is not the reason for their protective action. Separate experiments with the amnesia blockers Gln Phe Val Gly (SEQ ID NO: 2), Asp Phe Phe Val Gly (SEQ ID NO: 1), and Ala Ile Phe Thr (SEQ ID NO: 3) in weakly trained animals (Table 2) showed these substances not to have any memory-enhancing effects on retention of T-maze FAAT, indicating that amnestic effects of β-(12–28) were not being overcome by independent memory-enhancing effects of these substances.

TABLE 2

Effects of Asp Phe Phe val Gly (SEQ ID NO: 1), Ala Ile Phe Thr (SEQ ID NO: 3) and Gln Phe Val Gly (SEQ ID NO: 2) on retention of T-maze FAAT measured in weakly trained mice (groups of 14 each)[1]

| Peptide | Trial to criterion, no (mean ± SEM) | P-value for comparison with vehicle |
|---|---|---|
| Vehicle alone | 9.07 ± 0.25 | — |
| Asp Phe Phe Val Gly | 9.14 ± 0.32 | — |
|  |  | NS[2] |
| Ala Ile Phe Thr | 9.43 ± 0.30 | NS |
| Gln Phe Val Gly | 9.64 ± 0.28 | NS |

[1]This paradigm is designed to measure the extent of enhancement, if any, over that found with vehicle alone (0.001% DMSO in saline). None was observed.

[2]NS = not significant.

Esters and Amides of Ala Ile Phe Thr (SEQ ID NO: 3), Asp Phe Phe Val Gly (SEQ ID NO: 1) and Gln Phe Val Gly (SEQ ID NO: 2) as Antagonists of Amnestic effects of Aβ. The most likely additional related substance is to synthesize and administer would be esters and amides of the three active peptides (SEQ ID NOS: 1, 2 and 3) in which the carboxyl group of each of them is esterified or amidated.

The peptidic esters preferably have the structural formula:

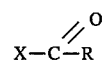
I.

in which X is a peptide, SEQ ID NO: 1, SEQ ID NO: 2 or SEQ ID NO: 3 and R is a straight or branched chain alkyl group having one to eighteen carbon atoms, an aromatic group, e.g., a substituted or unsubstituted phenyl, napthyl or anthracyl group, a heterocyclic group, e.g., a pyridine or imidazole group or a steroidal group, e.g., pregnenolone, dehydroepiandosterone, progesterone and or any biologically active steroid having an available hydroxyl group.

The peptidic amides have the structural formula:

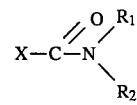
II.

in which X may be the same as X in Formula I and in which $R_1$ and $R_2$ are the same or different alkyl, aromatic, heterocyclic or steroidal group as in Formula I. Such substances may be more resistant to enzymatic attack than the parent peptides and could pass the blood-brain barrier more readily, whereupon they would be hydrolyzed to form, the effective peptide in the brain.

REFERENCES

1. Miller-Hill, B., et al., *Annu. Rev. Biochem.* 58:287–307 (1989)
2. Selkoe, D. J., *Science* 248:1058–1060 (1990)
3. Douglass, J., et al. Annu. Rev. Biochem. 53:665–715 (1984)
4. Scheller, R. H., et al., *Cell* 327-22 (1983)
5. Dyrks, Et., et al., *EMBO J.* 7:949–957 (1988)

6. Buxbaum, J. D., et al. *Proc.Natl.Acad.Sci.USA* 87:6003–6006 (1990)
7. Kang, J., et al., *Nature (London)* 325:733–736 (1987)
8. Shivers, B. D., et al., *EMBO J.* 7:1365–1370 (1988)
9. Allsop, D., et al. *Proc.Natl.Acad.Sci.USA* 85:2790–2794 (1988)
10. Glenner, G. G., et al. *Biochem. Biophys. Res. Commun.* 122:1131–1135 (1984)
11. Glenner, G. G., et al. *Biochem. Biophys. Res. Commun.* 120:885–890 (1984)
12. Masters, C. L., et al. *Proc. Natl.Acad.Sci.USA* 82:4245–4249 (1985)
13. Kitaguchi, N., et al. *Nature (London)* 331:530–532 (1988)
14. Selkoe, D. J., *Neurobiol. Aging* 10:387–395 (1989)
15. Blessed, G., et al. *Br.J.Psychiatry* 114:797–811 (1968)
16. Wilcock, G. K., et al. *J. Neurol. Sci.* 56:343–356 (1982)
17. Mann, D. M. A., et al. *Neurosci. Lett.* 56:51–55 (1982)
18. Davies, L., et al., *Neurology* 38:1688–1693 (1988)
19. Kirschner, D. A., et al., *Proc. Natl. Acad. Sci. USA* 84:6953–6957 (1987)
20. Kirschner, D. A., et al., *Proc. Natl. Acad. Sci. USA* 83:503–507 (1986)
21. Castano, E. M., et al., *Biochem. Biophys. Res. Commun.* 141:782–789 (1986)
22. Hyman, B. T., et al., *Science* 225:1168–1170 (1984)
23. Bondareff, W., et al. *Neurology* 32:164–168 (1989)
24. Snow, A. D., et al., *Neurobiol. Aginig* 10:481–497 (1989)
25. Flood, J. F., et al. *Proc. Natl. Acad. Sci. USA* 88:3363–3366 (1991)

I claim:

1. A peptide having the sequence of SEQ ID NO: 1, SEQ ID NO: 2 or SEQ ID NO: 3.

2. An ester or an amide of a peptide as defined by claim 1.

3. A peptide ester having the structure Formula I.

4. A peptide amide having the structure Formula II.

* * * * *